United States Patent [19]

Purvis

[11] Patent Number: Plant 5,866

[45] Date of Patent: Jan. 27, 1987

[54] *NERIUM OLEANDER* CV. MONVIS

[75] Inventor: Richard L. Purvis, Anaheim, Calif.

[73] Assignee: Monrovia Nursery Company, Azusa, Calif.

[21] Appl. No.: 752,822

[22] Filed: Jul. 8, 1985

[51] Int. Cl.[4] ..... A01H 5/00
[52] U.S. Cl. ..... Plt./54
[58] Field of Search ..... Plt./54

[56] References Cited

U.S. PATENT DOCUMENTS

P.P. 4,836 4/1982 Aldridge ..... Plt./54

*Primary Examiner*—James R. Feyrer

[57] ABSTRACT

A new and distinct selection of *Nerium oleander* L. shrub (popularly known as Oleander) which shall be referred to hereinafter as *Nerium oleander* cultivar Monvis. *Nerium oleander* cultivar Monvis differs distinctively from other oleanders by a unique combination of large bright rose flowers, an abundance of flowers, early flowering and a dense compact growth habit.

2 Drawing Figures

DISCOVERY

This invention relates to a new and distinct selection of *Nerium oleander,* a member of the Apocynaceae or dogbane family. *Nerium oleander* cv. Monvis resulted as a seedling of my hybridizing work which was grown on at 936 South Siet Street, Anaheim, Calif. in May of 1976. The plant to date is known to exist only within the boundaries of the above address and Monrovia Nursery, 18331 E. Foothill Boulevard, Azusa, Calif. and has not been offered for sale or described in any publication.

REPRODUCTION

My new selection has been strictly asexually reproduced by cuttings at Monrovia Nursery Company. The distinct phenotypic characteristics of this selection that set this plant apart from other oleander plants could be lost genetically through sexual reproduction. Therefore, propagation is restricted to asexual reproduction and sexual reproduction is prohibited.

BRIEF DESCRIPTION OF THE DRAWINGS

The accompanying illustrations show a typical specimen of the plant according to this invention and are depicted in color as nearly true as possible.

The above photo, FIG. 1, shows the original specimen of the selected plant exhibiting the heavy abundance of flowers causing the foliage to droop due to the weight of flowers. Also exhibited in this photo is the natural dense, compact habit as this plant has never been pruned on the upper portion, only the lower branches.

FIG. 2, depicts a close up of the large 3 inch diameter, bright rose flowers.

DESCRIPTION

Below is a detailed description of the new *Nerium oleander* cv. Monvis, the color terminology is from The British Horticultural Colour Charts.

Overall size and habit: Evergreen, dense, after 9 years plant is approximately 7 feet in height and 6 feet in width.

Foliage:
- *Size.*—Length 11.8 cm–14.8 cm; width 1.8–2.1 cm.
- *Shape.*—Narrowly elliptic.
- *Color.*—Upper: Parsley Green 00962. Lower: Spinach Green 0960/3.
- *Margins.*—Entire.
- *Texture.*—Coriaceous.
- *Arrangement.*—Whorls of 3.
- *Pubescence.*—Glabrous.
- *Petioles.*—5–6 mm.

Flower: Terminal branching cymes.
- *Size.*—Diameter 7 to 8 cm.
- *Shape.*—Corolla funnelform; corolla tube cylindrical campanulate throat with 5 broad laciniate teeth; 5 lobes spreading and twisting clockwise.
- *Color.*—Petals — Rose Bengal 25. Laciniate Teeth — Rose Bengal at tips fading to lighter colors at throat with dark longitudinal stripes.
- *Corolla lobes.*—3.5 to 4 cm long. 2 to 2.2 cm wide.
- *Calyx.*—5 lobed, 4–6 mm.
- *Peduncle.*—4–5 mm in length.

I claim:

1. A new and distinct selection of *Nerium oleander* as substantially shown and described herein, that is characterized particularly as a novelty by the unique combination of large bright rose flowers, early flowering and a dense compact growth habit.

* * * * *

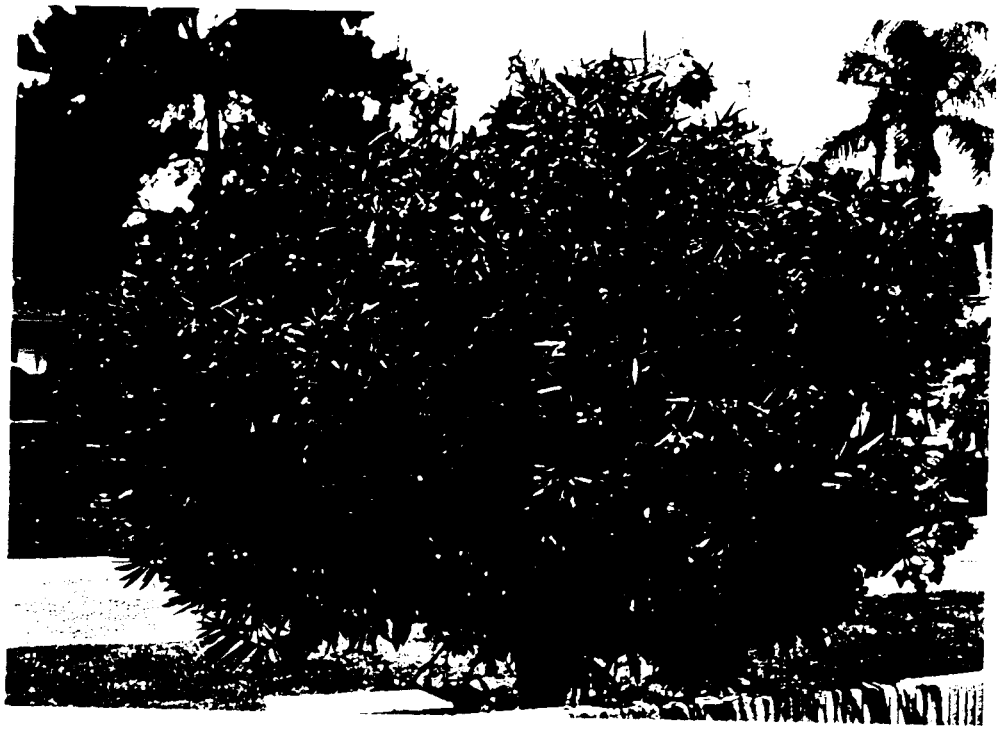
FIG. 1 SELECTION
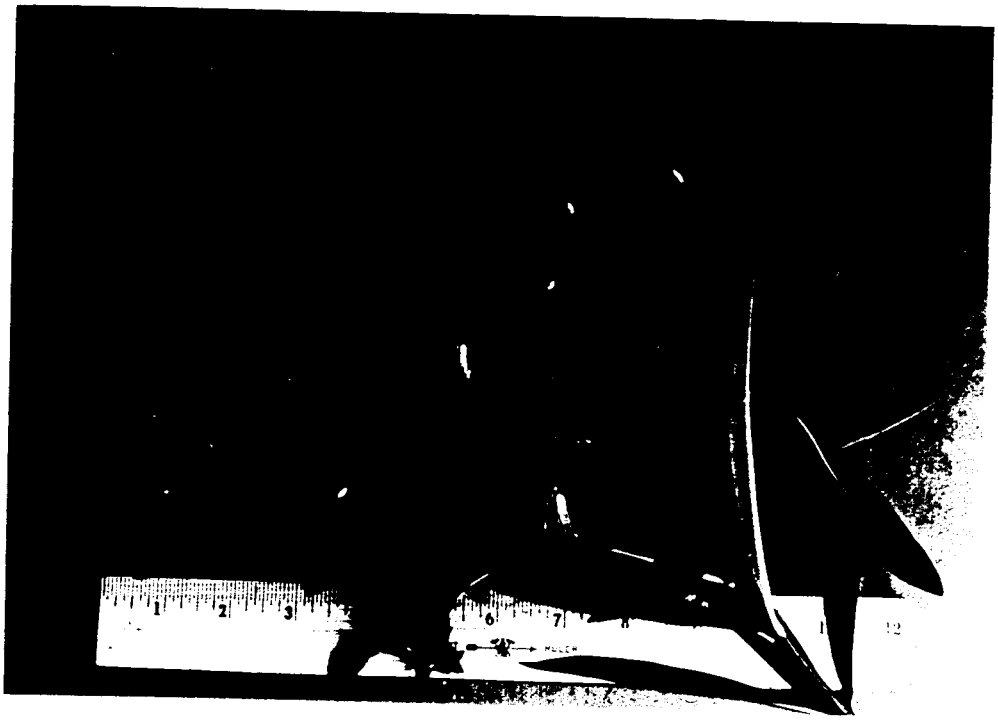
FIG. 2 SELECTION